United States Patent [19]
Ivarsson et al.

[11] Patent Number: 6,127,183
[45] Date of Patent: Oct. 3, 2000

[54] MONITORING OF REFRACTIVE INDEX OF OPTICAL SENSOR FOR DETERMINATION OF SURFACE STRUCTURE CHANGES

[75] Inventors: Bengt Ivarsson, Bälinge; Esa Stenberg, Uppsala, both of Sweden

[73] Assignee: Biacore AB, Sweden

[21] Appl. No.: 09/043,006

[22] PCT Filed: Aug. 30, 1996

[86] PCT No.: PCT/SE96/01074

§ 371 Date: Aug. 26, 1998

§ 102(e) Date: Aug. 26, 1998

[87] PCT Pub. No.: WO97/09618

PCT Pub. Date: Mar. 13, 1997

[30] Foreign Application Priority Data

Sep. 1, 1995 [SE] Sweden .................................. 9503028

[51] Int. Cl.⁷ .................................................. G01N 13/71
[52] U.S. Cl. .............................. 436/34; 436/164; 356/445
[58] Field of Search ................................ 436/34, 86, 164; 356/445

[56] References Cited

U.S. PATENT DOCUMENTS 5,313,264  5/1994  Ivarsson et al. ........................... 356/73
5,359,681  10/1994  Jorgenson et al. ......................... 385/12

OTHER PUBLICATIONS

Fägerstam et al., "Biospecific interaction analysis using surface plasmon resonance detection applied to kinetic, binding site and concentration analysis," *Journal of Chromatography 597*: 397–410, 1992.

Glaser, "Antigen–Antibody Binding and Mass Transport by Convection and Diffusion to a Surface: A Two–Dimensional Computer Model of Binding and Dissociation Kinetics," *Analytical Biochemistry 213*: 152–161, 1993.

Morton et al., "Interpreting Complex Binding Kinetics from Optical Biosensors: A Comparison of Analysis by Linearization, the Integrated Rate Equation, and Numerical Integration," *Analytical Biochemistry 227*: 176–185, 1995.

Rogers et al., "Pharmacological specificity of a nicotine acetylcholine receptor optical sensor," *Biosensors & Bioelectronics 6*: 507–516, 1991.

Thompson et al., "Total internal reflection fluorescence microscopy: application to substrate–supported planar membranes," *European Biophysics Journal 22*: 367–378, 1993.

Goldschmidt, "Measurement and Interpretation of Optical Properties at High Temperatures," *SPIE 452*: 110–117, 1983.

Arakelian et al., "Excitation Of Nonlinear Surface Electromagnetic Waves In The Prism–Metal Film–Nematic Liquid Crystal System," *Physics Letters A 118*(5): 254–259, 1986.

Salamon et al., "Assembly and molecular organization of self–assembled lipid bilayers on solid substrates monitored by surface plasmon resonance spectroscopy," *Biochimica et Biophysica Acta 1195*: 267–275, 1994.

Pollard and Sambles, "The Time–Dependence Of The Growth Of Thin Organic Liquid Layers On A Gold–Surface, Studied By Surface–Plasmon Polariton Techniques," *Optics Communications 64*(6): 529–533, 1987.

Gruen et al., "Determination of relative binding affinity of influenza virus N9 sialidases with the Fab fragment of monoclonal antibody NC41 using biosensor technology," *Eur. J. Biochem. 217*: 319–325, 1993.

*Primary Examiner*—Jeffrey Snay
*Attorney, Agent, or Firm*—Seed Intellectual Property Law Group

[57] ABSTRACT

The invention relates to a method of analysing a chemical or physical interaction taking place in a film layer at an optical sensor surface when the film layer is contacted with a fluid sample containing a species capable of interacting with the film layer, wherein the interaction is monitored by determination of the refractive index of the film layer through a light-intensity signal producing technique by measuring the relationship between a parameter of the incident and/or reflected light and one of the minimum, the maximum and the centroid of the light intensity signal curve. The method is characterized by also monitoring the variation of the light intensity signal value at said minimum, maximum or centroid with time to determine at least one of (i) the degree of homogeneity of sample species concentration in the sensed film layer volume to determine therefrom when the interaction is mass transport limited and when the interaction is kinetically controlled, a varying light intensity signal level indicating mass transport limitation and a stabilized light intensity signal level indicating kinetic control; and (ii) the degree of resulting homogeneity/heterogeneity in the sensed film layer volume during or after the interaction, a changed stabilized light intensity signal level indicating and corresponding to the degree of a change in homogeneity/heterogeneity.

22 Claims, 8 Drawing Sheets

MONITORING OF REFRACTIVE INDEX OF OPTICAL SENSOR FOR DETERMINATION OF SURFACE STRUCTURE CHANGES

FIELD OF THE INVENTION

The present invention relates to an improved method of analysing physical or chemical interactions taking place in a film layer at an optical sensor surface by means of refractive index determination through light intensity signal producing techniques.

BACKGROUND OF THE INVENTION

Recently, the interest for surface sensitive measuring techniques has increased markedly as several so-called label-free optical techniques have been developed for measuring and quantifying biomolecular interactions. A so far frequently used such optical technique is based on surface plasmon resonance, hereinafter often referred to as SPR.

When light travels from an optically denser medium (i.e. having a higher refractive index) to a less dense medium (i.e. having a lower refractive index), total internal reflection (TIR) occurs at the interface between the two media if the angle at which the light meets the interface is above a critical angle. When TIR occurs, an electromagnetic "evanescent wave" propagates away from the interface into the lower refractive index medium.

If the interface is coated with a thin layer of certain conducting materials (e.g. gold or silver), the evanescent wave may couple with free electron constellations, called surface plasmons, at the conductor surface. Such a resonant coupling occurs at a specific angle of the incident light, absorbing the light energy and causing a characteristic drop in the reflected light intensity at that angle. The surface electromagnetic wave creates a second evanescent wave with an enhanced electric field penetrating into the less dense medium.

The resonance angle is sensitive to a number of factors including the wavelength of the incident light and the nature and the thickness of the conducting film. Most importantly, however, the angle depends on the refractive index of the medium into which the evanescent wave of the surface plasmon wave propagates. When other factors are kept constant, the resonance angle is thus a direct measure of the refractive index of the less dense medium, the angle being very sensitive to refractive index changes in the medium. For a detailed description of the dielectric equations describing this dependence it may be referred to Kretschmann, E., Z. Phys. B241, 313 (1971).

The SPR evanescent wave decays exponentially with distance from the interface, and effectively penetrates the lower refractive index medium to a depth of approximately one wavelength. Therefore, only changes in refractive index very close to the interface may be detected.

If the metal film is covered with an appropriate sensing layer (e.g. an antibody) capable of specific interaction with a molecule (e.g. an antigen) present in a fluid sample contacted with the sensing layer, SPR based chemical sensors may be constructed, the interaction at the sensor surface changing the solute concentration and bound surface concentration and thus the refractive index within the penetration range of the evanescent wave. A variety of SPR-based chemical sensors have been developed wherein the change of the reflectance curve (reflected light intensity versus angle of incidence or wavelength) with time is measured, which change is correlated to the surface refractive index.

Different techniques may be used for bringing the light to interact with the sensor surface. A commonly used detection system is based on the Kretschmann configuration (Kretschmann and Raether, Z. Naturforsch. Teil A 23: 2135–2136, 1968). In this configuration a thin layer of the reflective metal (gold or silver) is deposited on the base of a prism and TM polarized, monochromatic light is coupled by the prism to the SPR-wave.

An example of a commercial biosensor system constructed on the basis of the Kretschmann configuration is BIAcore™, marketed by Pharmacia Biosensor AB (Uppsala, Sweden). This biosensor system incorporates a Kretschmann configuration-based SPR-detection system with a microfluidic system to control the flow of reagents required in the analyses. With this apparatus, biomolecular interactions occurring at the sensor surface may be monitored in real time. The apparatus and theoretical background thereof has been fully described by Jonsson et al., 1991, BioTechniques 11, 620–627. It is also referred to our U.S. Pat. No. 5,313,264.

When monitoring the biomolecular interactions, the development of the SPR-response, or surface film refractive index, with time is followed. From this relationship not only the biomolecule analyte concentration may then be determined but also kinetic parameters, such as association and dissociation rate constants for the interaction of the biomolecule with the sensor surface.

As an alternative to the reflectance minimum angle, the angle of the centroid of the reflectance curve may be monitored.

Rather than measuring the incident light angle where SPR (i.e. reflectance minimum) occurs, some SPR sensors, as already mentioned above, introduce the light at a fixed angle and measure the wavelength at which SPR takes place (see e.g. U.S. Pat. No. 5,359,681), SPR in both cases, however, representing a reflectance minimum of the reflectance curve.

When studying kinetic parameters, it is, of course, important to know when the interaction at the surface is mass transport limited and when it is reaction-kinetically controlled. This may not readily be determined from the above-mentioned refractive index versus time curve, and there is therefore always a risk of an incorrect estimate of kinetic constants. Further, it may not be readily determined from the refractive index versus time curve whether the interaction at the surface has caused any structural change of the surface resulting in a heterogeneity.

In other contexts than the chemical SPR sensors, parameters such as the intensity of the reflectance minimum ($R_{min}$) and the halfwidth ($\Phi_{1/2}$) of the reflectance curve have been studied.

Pockrand, I., Surface Science, vol. 72, p. 577–588 (1978) describes the influence of thin dielectric coatings on the properties of surface plasma oscillations propagating along a metal surface using an attenuated total reflection (ATR) arrangement to excite SPR. A general shift and a broadening of the resonance curve are observed. The depth of the resonance $R_{min}$ is unaffected by transparent coatings, whereas it is strongly dependent on the thickness of an absorbing coating.

Fontana, E., Pantell and Moslehi, Applied Optics, vol. 27, (1988) p. 3336 characterizes dielectric-coated metal mirrors using surface plasmon spectroscopy. Analytical expressions for SPR angle shift, halfwidth and reflectivity minimum are described.

Chu, K. C., et al., Mol. Cryst. Liq. Cryst., vol. 59, p. 97–108, (1980) discloses a study of isotropic-nematic phase transition of 4-cyano-4'-n-pentylbiphenyl on gold as a function of temperature by surface plasmon resonance technique. Changes in reflectance curve halfwidth and the occurrence of two reflective dips were observed. One of the two resonant angles corresponds to the refractive index of the isotropic phase, and the other to the refractive index of the nematic phase. The relationship between the dip depths of the "double dip reflectivity curve" was used as a measure of the fraction of the medium in each of the two phases.

Pollard, J. D., and Sambles, J. R., Optics Communications, vol. 64, p. 529–533 (1987) describes the analysis of the time-dependence of the SPR reflectance curve parameters, reflectance minimum angle, reflectance minimum depth, and reflectance curve width to study the lateral extension of the two phases of a condensed liquid, i.e. as droplets and as a homogeneous film, respectively. The existence of two distinct refractive indices in different parts of an illuminated gold surface gave two reflectance curves which together gave a reflectance curve with two minima, the depth of the respective minimum corresponding to the mutual degree of coverage of the gold surface.

Rothenhäusler and Knoll, Surface Science, vol. 191, p. 585–594, (1987) discloses reflectivity versus angle scans in the Kretschmann ATR configuration of an silver-air interface with p-polarized laser light. If there is within the area of the laser spot on the sample film a step from one thickness to another, two resonance minima are obtained, each at an angle corresponding to one of the two "infinite" layer structures. The intensities of the resonance minima depend on the relative area fraction of the two different interfaces covered by the laser spot.

Rothenhäusler and Knoll, Appl. Phys. Lett., vol. 51, p. 783–785, (1987) discloses the use of SPR in combination with diffraction to study a discrete film of two media with different layer structures. The mutual relationship between the reflectance minima of two simultaneous SPR's is used to determine the degree of surface coverage for the respective media.

Yeatman and Ash, SPIE, vol. 897, p. 100–107, (1988) p. 107 discloses a technique for SPR microscopy for studying lateral structure (surface heterogeneity distribution) in biological monolayers and other superimposed layers. It is proposed that the position, width and depth of the reflectance minimum be measured to permit different contrast mechanisms to be separable due to their different relative effects on the three parameters.

Zhang, Y. et al, Surface Sci., vol. 184, p. 214–226, (1987) describes the use of surface plasmon oscillations for the investigations of the kinetics of adsorption of a polystyrene film onto a metallic surface. The resonance angular shift, the halfwidth of the dip and the value of the resonance minimum is used for determining the characteristics of the adsorbed layer.

Silin, V. I., et al., Optics Communications, vol. 97, p. 19–24, (1993) discloses broadening of the surface plasmon line in a biosensor system in which an immunologic reaction of the antigen-antibody type takes place due to irregularities, roughness or even a discrete structure of the studied film, resulting in a sharp decrease of the sensitivity in the measurement of the reflectance curve minimum angle.

Salamon, Z., Wang, Y., Tollin, G. and Macleod, H., Biochimica et Biophysica Acta, 1195(2), p. 267–75 (1994) reports theoretical modelling for experimental surface plasmon resonance results to determine the thickness, refractive index, and extinction coefficient of self-assembled lipid bilayers, and to calculate the adsorbed mass and volume. From this calculated data the average steady state structure of the lipid layer is characterized. It is demonstrated that deposition of a lipid layer may change the SPR-reflectance curve so that (i) the position of the resonance minimum is shifted towards larger incident angles; (ii) the reflected light intensity at the resonance minimum is increased; and (iii) the SPR curve is broadened. The observation of only one resonance minimum indicates that the coverage of the silver surface of the sample molecules is homogeneous.

In summary, while as described above, it has been recognized in the prior art that the shape of the surface plasmon resonance curve may contain certain structural information on an SPR-probed solid or liquid film, measurement of the value (i.e. depth) of the reflectance minimum or the halfwidth of the reflectance curve have never been used in SPR-based biosensor applications for the monitoring of surface interactions. Nor has it been suggested that such reflectance curve information would be of any use therein.

SUMMARY OF THE INVENTION

One object of the present invention is to provide in the analysis of interactions taking place at an optical sensor by surface refractive index measurement, such as SPR, means for determining when an interaction is mass transport limited and when it is kinetically controlled.

Another object of the present invention is to provide in the analysis of an interaction taking place at an optical sensor by surface refractive index measurement, such as SPR, means for determining the degree of any heterogeneity in the sensed surface layer during or resulting from the interaction.

According to the present invention it has been found that the above and other objects and advantages may be achieved by, in addition to monitoring the refractive index variation at the surface by measuring the minimum, maximum or centroid of a light intensity signal curve, also monitoring the variation of the value of the light intensity signal at the minimum, maximum or centroid, and optionally also the halfwidth of the light intensity signal curve.

More particularly, it has been found that a varying signal intensity minimum or maximum level will represent mass transport limitation of the interaction at the surface, whereas a stabilized minimum or maximum level indicates kinetic control of the interaction. This will permit the kinetic constants to be measured more conveniently and with a substantially higher degree of accuracy than in the prior art methods.

Further, a changed (increased or decreased) stabilized minimum or maxiumum level will indicate that there is a resulting homogeneity/heterogeneity change in the sensed film. Hereby, for example, also the time and degree of a homogeneity/heterogeneity change in the sensed film may be accurately determined.

The present invention thus provides a method of analysing a chemical (including biochemical) or physical (including biophysical) interaction taking place in a film layer at an optical sensor surface when the film layer is contacted with a fluid sample containing a species capable of interacting with the film layer, wherein the interaction is monitored by determination of the refractive index of said film layer through a light-intensity signal producing technique by measuring the relationship between a parameter of the incident and/or reflected light and of one of the minimum, the maximum and the centroid of the light intensity signal curve. The method is characterized by, in addition to monitoring the refractive index, also monitoring the variation of the light intensity signal value at said minimum, maximum or centroid with time to determine at least one of (i) the degree of homogeneity of sample species concentration in the sensed film layer volume to determine therefrom when the interaction is mass transport limited and when the interaction is kinetically controlled, a varying light intensity signal level indicating mass transport limitation and a stabilized light intensity signal level indicating kinetic control; and (ii) the degree of homogeneity/heterogeneity in the sensed film layer volume during or after the interaction, a changed stabilized light intensity signal level indicating and corresponding to the degree of a change in homogeneity/heterogeneity.

The light-intensity signal producing technique used for measuring the refractive index may be selected from a variety of established optical methods, including conventional reflectometry, reflection ellipsometry, reflection interferometry and resonant guided mode detection in a waveguide. While these methods are based on the detection of a reflectance minimum, this minimum may also be manifested as a maximum in the light intensity signal, e.g. by relating the reflected intensity from differently polarized light.

In conventional reflectometry, the sensor surface reflectivity (absolute value of reflection constants) of light is measured through the reflected light intensity as a function of a suitable parameter, usually angle of incidence and/or wavelength. The reflection mode may be internal (involving an evanescent wave), or external. Among internal reflection methods may be mentioned those based on surface plasmon resonance (SPR), Brewster angle, and critical angle. External reflection methods include Brewster angle detection.

In reflection ellipsometry, the phase shift (phase of reflection constants) introduced by the sensor surface on the polarization state of the reflected light is measured through the detected light intensity as a function of a suitable parameter, usually polarizer (analyser) angle, compensator angle, angle of incidence, or wavelength. The reflection mode may be internal (evanescent wave ellipsometry) or external (conventional ellipsometry).

In reflection interferometry, the phase shift (phase of reflection constants) introduced by the sensor surface and which changes the intensity or polarization state of the reflected light is measured through the detected light intensity as a function of a suitable parameter, usually polarizer (analyser) angle, compensator angle, angle of incidence, or wavelength. The reflection mode may be internal (involving an evanescent wave), or external.

In resonant guided mode detection in a waveguide, the mode coupling introduced by the sensor surface and which changes the transmission of the light via its absorption or phase shift is measured through the detected light intensity as a function of a suitable parameter, usually angle of incidence or wavelength. The reflection mode is internal (involving an evanescent wave). Methods using this detection technique include those based on frustrated total reflection (resonant cavity).

The light may interact with the sensor surface through transmission, grating-coupling, or coupling via frustrated total internal reflection (evanescent wave coupling), such as in resonant mirror devices.

The method of the invention may, for example, be performed with a combination of at least two wavelengths and a fixed incident angle. As another example, a combination of at least two wavelengths and at least two incident angles may be used. In another example, a continuous scan of a predetermined incident angle or wavelength range is used.

As still another example the monitoring may be performed using at least two different polarisation states and fixed incident angle and wavelength. In another example, a continuous scan of a predetermined polarisation state range is used.

While the fluid sample may in principle be a gas, it is usually a liquid.

The method of the invention may, of course, be used in the monitoring of two or more sensor surfaces simultaneously as is per se known in the art.

One embodiment of the present invention comprises determining from the monitoring of the reflectance minimum or maximum value the time interval or intervals when the interaction at the surface is kinetically controlled, and from the relationship between refractive index and time measured during this interval or intervals determining the association and/or dissociation constants for the interaction of the sample species with the surface layer. Preferably, such kinetic constant determination is initiated automatically when it is determined that the interaction is kinetically controlled, for example, by modification of software used in the evaluation of the constants.

Another embodiment of the invention comprises determining from the monitoring of the reflectance minimum or maximum value the time interval when the interaction at the surface is mass transfer limited, and from the relationship between refractive index and time measured during this interval or intervals determining the concentration of the sample species. Many times it is desirable to determine both concentration and a kinetic constant or constants.

The homogeneity/heterogeneity of the film layer usually relates to one or more of the physical condition (concentration structure, protein aggregates, crystallinity, phase, gas), the thermodynamic condition (temperature, surface energy) and the chemical condition (pH, ionic strength, charge) of the film layer.

Two different cases may be identified depending on the size of the sample (analyte) molecule:

(i) A macromolecular sample in solution (e.g. protein) binds to/reacts with the immobilized film which is activated and thereby changed to be more heterogeneous or more homogeneous. In the first case, the reflectance minimum is stabilized at a higher level than before the sample addition, whereas in the latter case the reflectance minimum is stabilized at a lower level, as will be described in more detail below. Homogeneity of the sample binding will then have to be detected on a reference sensor surface. Thereby, a measured and quantified homogeneity change may be attributed to the immobilized film.

(ii) A low-molecular sample in solution (e.g. drugs, small molecules produced by cells in solution outside the sensor volume) binds to/reacts with the immobilized film which is activated and thereby changed to be more heterogeneous or more homogeneous. These small molecules are, however, not capable of giving any significant refractive index change by themselves, but may activate a significant structural change of a macromolecular immobilized film.

Often it may be valuable to determine the sample species concentration related to a particular change in homogeneity/heterogeneity of the film layer. Determination of homogeneity/heterogeneity may also be used as a quality control of a pre-immobilized reactant concentration or structure with regard to homogeneity.

Particularly, heterogeneity in the surface film layer is selected from protein aggregates caused by precipitation, agglutination or flocculation reactions; membrane complexes, such as biological cells and cell membrane fragments; macromolecular product complexes caused by enzymatic reactions; and cellular product complexes.

A stability test of a protein solution may be performed by simultaneously determining bound protein concentration and heterogeneity in the bound protein film due to protein aggregates in the sample.

When the heterogeneity consists of membrane complexes, a simultaneous determination may be made of bound sample concentration and related binding or release of particulate sample, such as biological cells or cell membrane fragments.

When the heterogeneity consists of macromolecular product complexes, a simultaneous determination may be made of bound sample concentration and related enzymatic production, activation or inhibition, such as coagulation, fouling, enzymatic cascade reactions (such as in the blood coagulation system or the immunological complement system).

When the heterogeneity consists of cellular adhesion distribution or cellular product complexes, a simultaneous determination may be made of either sensor surface bound sample concentration or solution concentration, and related cellular adhesion distribution, like proliferation or degradation, or cellular molecule production.

Monitoring of also the halfwidth of the light signal intensity curve in question may provide additional information on the state of homogeneity/heterogeneity within the sensed surface volume.

In the case of an internal reflection based method, data measured at a number of wavelengths may be used to determine the state of homogeneity/heterogeneity in the direction of the penetration depth of the evanescent wave, the penetration depth varying with wavelength.

In the following the invention will be described in more detail primarily with regard to SPR detection, reference being made to the accompanying drawings.

BRIEF DESCRIPTION OF THE DRAWINGS

FIG. 2b is a plot of calculated reflectance vs angle of incidence curves for three different refractive indices for a two-phase film model corresponding to the interaction in FIG. 2a;

FIG. 3b is a plot of calculated reflectance vs angle of incidence curves for three different refractive indices for a two-phase film model corresponding to the interaction in FIG. 3a;

FIG. 4b is a plot of calculated reflectance vs angle of incidence curves for four different refractive indices for a two-phase film model corresponding to the interaction in FIG. 4a;

FIG. 4c is a plot of calculated reflectance vs angle of incidence curves for four different refractive indices for a three-phase film model corresponding to the interaction in FIG. 4a.

DETAILED DESCRIPTION OF THE INVENTION

Figure 1:
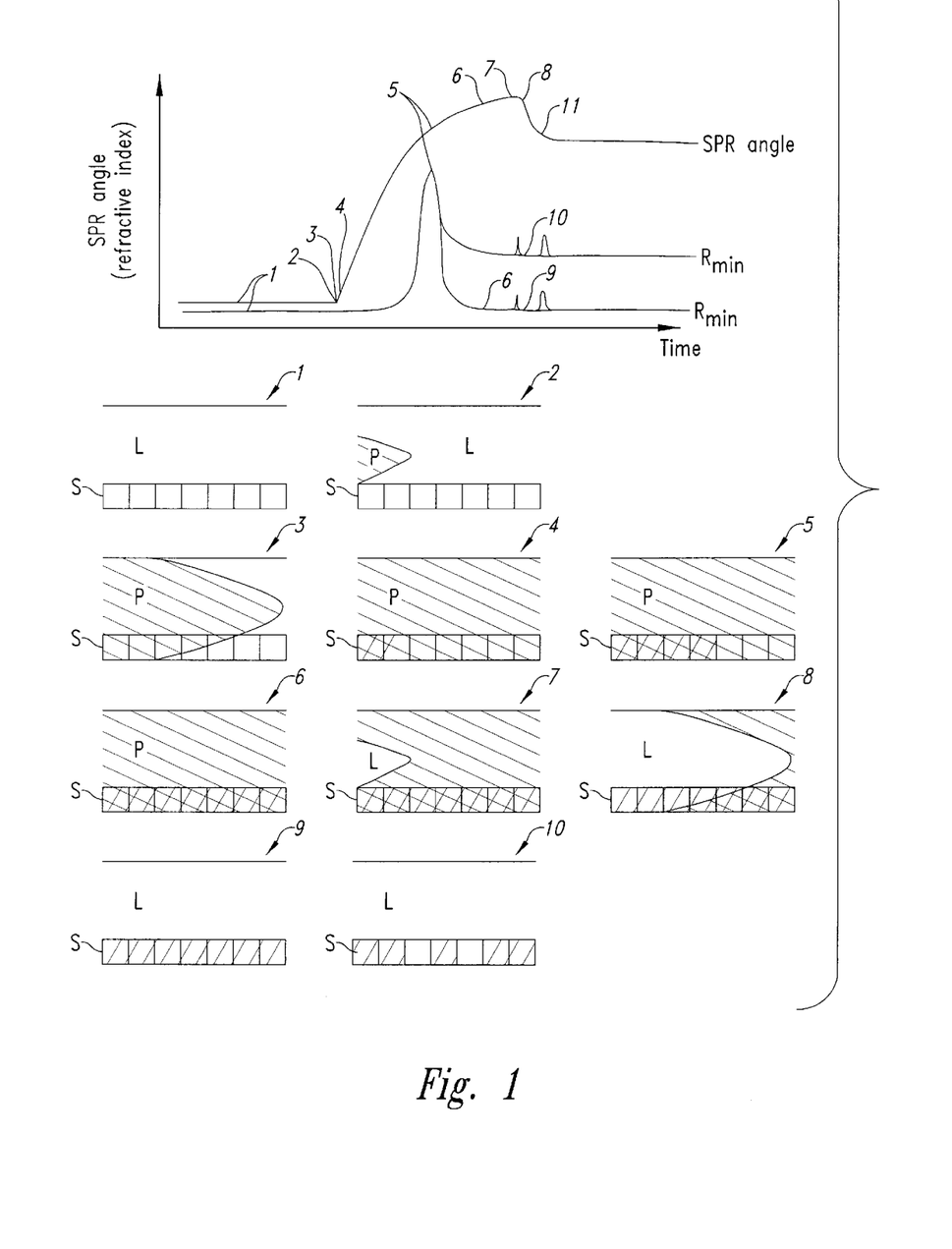
FIG. 1 shows (i) a schematic overlay plot of a sensorgram (SPR response vs time) and a reflectance minimum vs time curve for SPR measurements of surface interactions, and (ii) a number of schematic sectional views of a flow cell illustrating different states in the flow cell corresponding to defined parts of the sensorgram and the reflectance minimum curves.

In FIG. 1 is illustrated schematically in overlay format a typical SPR derived reflectance curve (SPR response, or resonance angle, versus time curve), or sensorgram, and a corresponding reflectance minimum ($R_{min}$) curve for the interaction of an analyte-containing sample solution with surface-immobilized reactant in a flow-cell, e.g. as obtained with a BIAcore™ system (Pharmacia Biosensor AB, Uppsala, Sweden). The analyte is, for example, an antibody and the immobilized reactant an antigen, or vice versa.

Below the curve diagram are shown a number of schematic cross-sections of the flow-cell, each designated by a numeral and representing different phases of the passage of the sample through the flow cell. The point on the sensorgram (SPR angle) and reflectance minimum ($R_{min}$) curve, respectively, that corresponds to a respective flow cell section is indicated by the same numeral as the flow cell section. The monitored sensing surface volume (containing the reactant), or sensor volume, which corresponds to the penetration depth of the evanescent wave, say $\approx 0.7$ $\mu$m, is designated by the letter S in the flow cell sections. The bottom part of the sensor volume contains a reaction layer, or matrix, (e.g. with a depth of about 100 nm) where the reactants are immobilized (not shown).

Numeral 1 designates the base line of the two curves, corresponding to the flow cell state prior to the introduction of the sample solution and with only solvent passing through the cell. The refractive index of the sensor volume, which for illustration may be said to be 1.335, is defined by the refractive indices of the solvent and the immobilized reactant.

At 2 (time=0) sample solution (solvent L plus dissolved sample P) starts entering the flow cell, no change of refractive index yet taking place.

At 3 the sample front has almost passed through the flow cell section and there is a high sample heterogeneity within the flow cell volume. The refractive index is still mainly determined by solvent and immobilized reactant, as the sample analyte is concentrated to the central core of the flow and has not diffused to the sensor volume to any great extent. While the refractive index starts to increase at this point, there is no notable effect on the reflectance minimum value.

At 4 ($t=t_1$) the flow cell is completely filled by sample solution (i.e. homogeneity with respect to sample solution), and analyte starts diffusing into the reaction layer and bind to the immobilized reactant. The reaction kinetics is mass transport limited, permitting the sample concentration within the sensor volume to be determined from this part of the reflectance curve as is well established in the prior art. The refractive index at this point may for illustration be e.g. about 1.336.

At 5 about half of the lateral extension of the sensor volume now contains bound reactant, resulting in a maximum heterogeneity of the sensor volume, which in turn causes a peak of the reflectance minimum value. At this stage the kinetics is dependent on both mass transport and reaction rate.

At 6 reactant has bound in the whole lateral extension of the sensor volume, and the analyte concentration within the sensor volume is homogeneous. The reflectance minimum value has decreased to base-line level. The reaction kinetics is now totally controlled by the reaction rate and the association rate constant may be determined from the sensorgram. The refractive index at this point is about 1.356.

At 7 (t=0) the whole sample plug has almost passed the flow cell and starts being replaced by wash solution L displacing unbound analyte.

At 8 the wash solution fills more than half the flow cell volume, and unbound or loosely bound analyte has been removed from about half sensor volume. This results in an instant heterogeneity in the sensor volume which causes the fast spikes observed in the reflectance minimum curve. The corresponding step in the sensorgram curve is caused by the bulk refractive index change. The refractive index at this point may e.g. for illustration be about 1.355.

At 9 (t=$t_1$ from the introduction of wash solution) there is a homogeneous reactant concentration within the sensor volume, and the reflectance minimum curve therefore returns to substantially the same baseline level as before the sample plug. Kinetically controlled dissocation of bound analyte has started and the dissociation rate constant may be calculated.

10 represents the corresponding point as 9 above for the case of a resulting higher degree of (permanent) heterogeneity within the sensor volume. The reflectance minimum curve does therefore not return to the original baseline level as at 9 but exhibits a raised baseline level. As at 9 above, the dissociation is reaction limited and the dissociation rate constant may be calculated.

At 11 (no flow cell section shown) there is significant desorption-in case of a high dissociation constant, resulting in a high sample heterogeneity within the sensor volume, which in turn causes a peak of the reflectance minimum curve. At this stage the kinetics is dependent on both mass transport and reaction rate. The sensorgram curve has now reached a lower level, corresponding to a refractive index of say about 1.350.

For an exemplary flow cell volume of 0.05 µl and a flow rate of 5 µl/min., the time $t_1$ when the liquid in the flow cell has been exhanged will be 0.6 seconds.

As demonstrated above, monitoring of the reflectance minimum ($R_{min}$) curve will indicate (i) when sample reaches the sensor surface and starts binding thereto, and (ii) when the sample plug has passed and is replaced by wash solution displacing sample. This applies both to the injection of sample into a carrier buffer flow and for segmented sample solution transport. Thus, it is possible to determine the time of simultaneous presence of buffer in a part of the sensed surface and of sample in another part of the sensed surface, and to relate this time to a corresponding SPR angle change.

This permits the measurement of kinetic constants to be repeatably synchronized to the time when the association and/or dissociation phases, respectively, are reaction rate controlled, that is when $R_{min}$ has passed the peak and is stabilized again. In an instrument like, for example, the above-mentioned BIAcore™ (Pharmacia Biosensor AB), means (e.g. software-based) may readily be designed to automatically provide for such synchronisation.

It is understood that the achieved increased accuracy in the determination of the above times for kinetic control of the association and dissociation phases will permit the kinetic constants to be determined with a considerably higher accuracy than before and with substantially less labour and trouble.

It has also been demonstrated above that simultaneously with the kinetics of SPR angle data, the degree of heterogeneity within the reactant film may be determined, for example as the result of the formation or dissolution of aggregates, crystallization, gas formation, temperature changes, phase or domain formation/resolution.

Thereby, for example, the time, specificity or surface concentration of the start of a homogeneity/heterogeneity change in the structure or state of the reactant film may be accurately determined, preferably automatically as above. Via the SPR angle-time curve, the corresponding specificity or surface concentration of the reactant film may be determined.

By such automatic measurement of the time, specificity and/or surface concentration for a quantified change of the homogeneity/heterogeneity within the volume sensed by the evanescent wave, the dependence of this reaction on the functional characteristics of a sample molecule may be determined with considerably higher accuracy than before and with less labour and trouble.

Of course, also the presence of permanent changes in the sensor film structure may readily be determined.

The experiments presented in the following-nonlimiting examples were performed with a BIAcore™ system, using a sensor chip CMS (a gold-plated glass slide supporting a carboxymethyldextran layer via a monolayer of long-chain hydrocarbons), both supplied by Pharmacia Biosensor AB, Uppsala, Sweden.

EXAMPLE 1

Soybean trypsin inhibitor (STI) (Sigma) was immobilized to the sensor chip surface according to the manufacturer's instructions. The surface was first activated with 1:1 N-ethyl-N'-(3-diethylaminopropyl)carbodiimide (EDC) and N-hydroxysuccinimide (NHS) for 3 minutes. 80 µg/ml of STI in 10 mM citric acid, pH 4.0, were then injected for 7 minutes. Deactivation of remaining activated groups was performed with ethanolamine-hydrochloride, pH 8.5, for 7 minutes. The surface was washed with HCl. The volumetric flow during the immobilization procedure was 5 µl/min. As buffer was used 10 mM Hepes, 150 mM NaCl and 0.05% BIAcore™ Surfactant P20, pH 7.4.

Kinetic analysis procedures with different concentrations of bovine pancreatic trypsin (BTP) (Sigma) were then run to determine kinetic constants for the interaction of BTP with the immobilized-STI. The volumetric flow rate was 10 µl/min.

The SPR response and the reflectance minimum, $R_{min}$, were monitored in the experiments. The point of time corresponding to the maximum value of $R_{min}$, $t(R_m)$, was extracted from the reflectance minimum curve. The sampling time was 0.2 seconds. Regeneration of the sensor surface was performed with HCl.

Figure 2A:
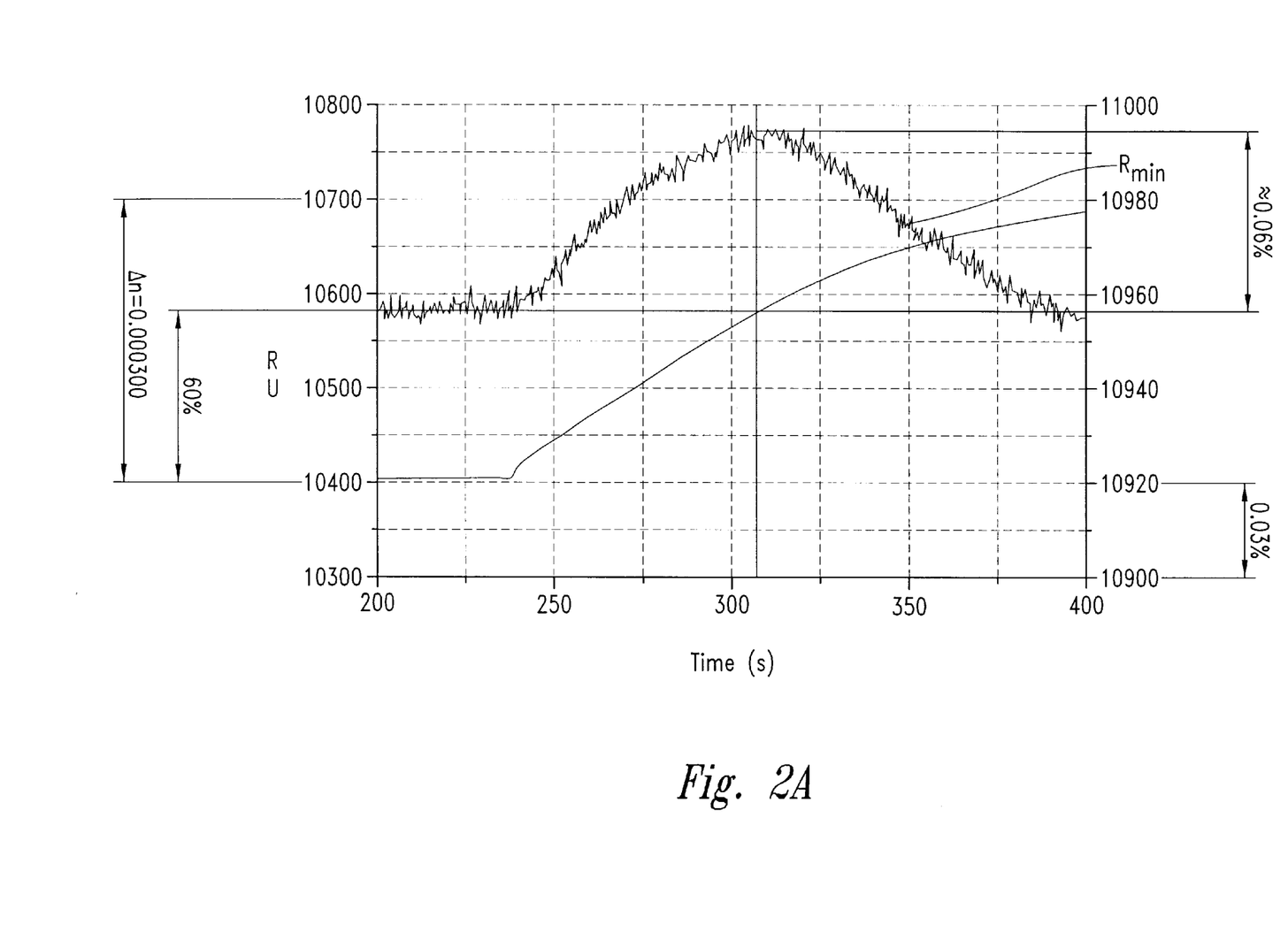
FIG. 2a is an overlay plot of a sensorgram (SPR response vs time) and a reflectance minimum vs time curve for the interaction of trypsin with immobilized trypsin inhibitor.

FIG. 2a shows a typical sensorgram part with associated $R_{min}$ curve, as obtained for 25 nM trypsin and a surface concentration of STI corresponding to 413 RU (Resonance Units–1000 RU corresponds to a 0.1° shift in SPR angle, or a refractive index change of 0.001). As appears from FIG. 2a, a maximum of the $R_{min}$ curve occurred during the association part (the illustrated part of the sensorgram). The $R_{min}$ change is about 0.06% coinciding with about 60% of the maximum change of the $R_{min}$ angle. $R_{min}$ then returns to approximately the level for sample-free solution.

Figure 2B:
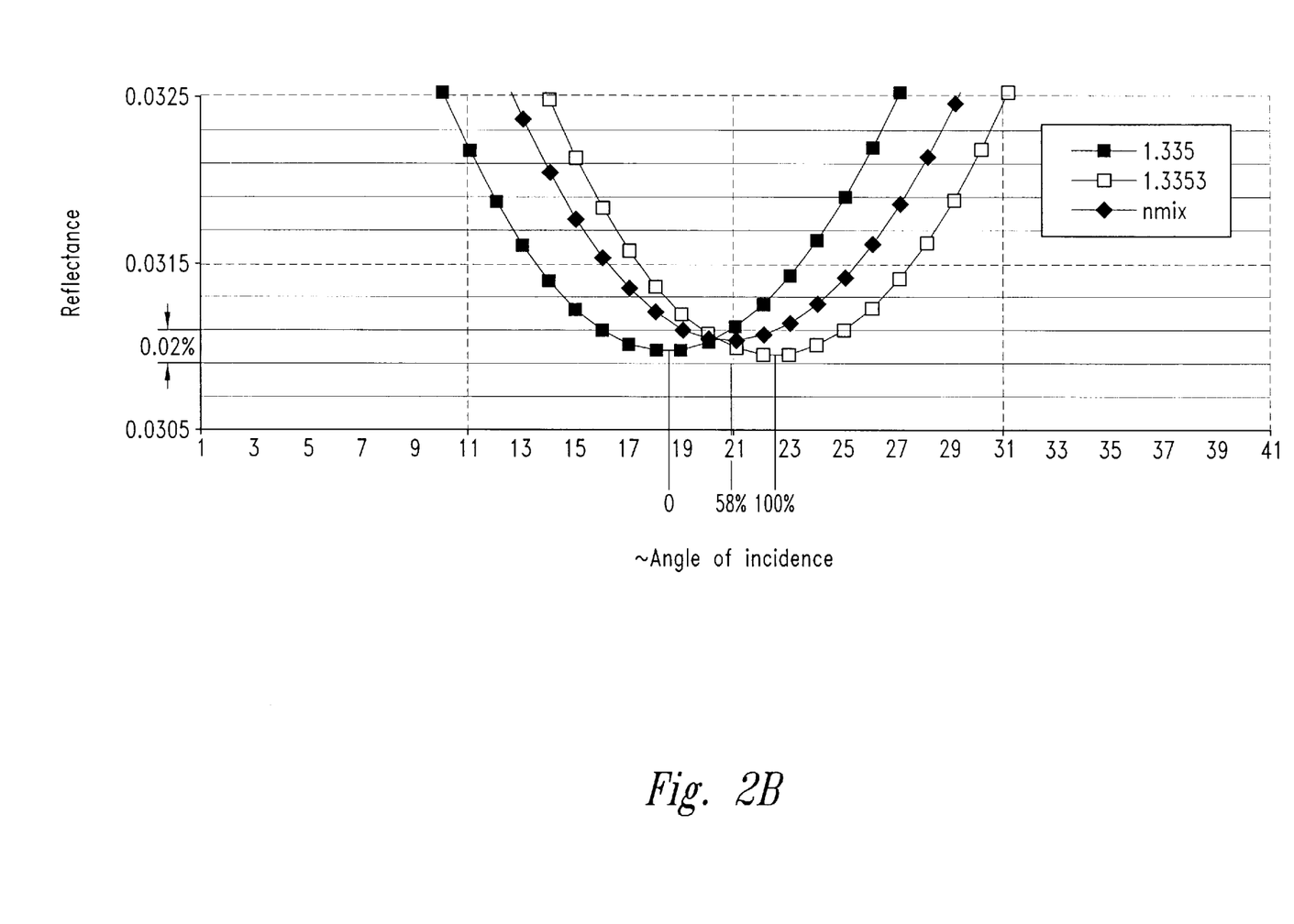

The above case represents the situation of two phases having close refractive indices/reflectance curves. A calculation of $R_{min}$ for a two-phase film model with a transition via a coverage 0.4 of phase 1, n=1.335, and coverage 0.6 of phase 2, n=1.3353, gave the results shown in FIG. 2b. The $R_{min}$ peak value was about 0.02%, coinciding with about 58% of the maximum change of the $R_{min}$ angle corresponding to a coverage 1.0 of phase 2.

From the analyses data it could be determined that the occurrence of the mass transfer/kinetically controlled break point correlated to the time event when $R_{min}$ had passed the maximum value and returned to a stabilized level. By monitoring the $R_{min}$ value together with the sensorgram the time value corresponding to the boarder between mass transfer controlled and kinetically controlled interaction may thus be determined. Feeding this time value into the evaluation scheme will therefore have the potential to simplify and improve the association and dissociation rate constants calculation.

EXAMPLE 2

Figure 3A:
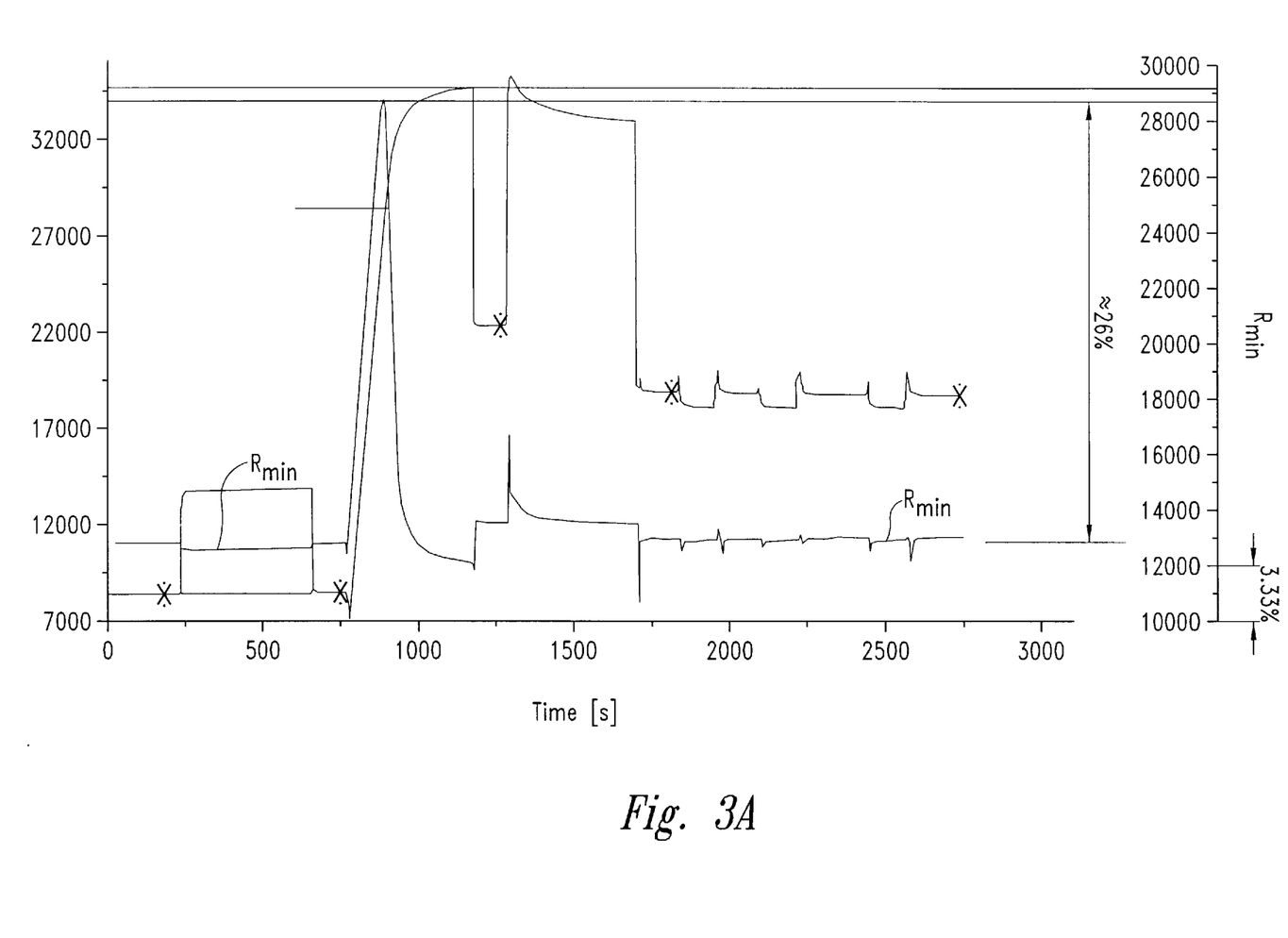
FIG. 3a is an overlay plot of a sensorgram (SPR response vs time) and a reflectance minimum vs time curve for the adsorption of rabbit antimouse IgG.

In analogous manner to Examples 1 and 2, the immobilization of rabbit antimouse IgG (RAMFc) onto a sensor surface by adsorption was studied at a flow rate of 5 μl/min. The sensorgram and the reflectance minimum ($R_{min}$) curve obtained are shown in FIG. 3a. As appears from the figure, the peak of the $R_{min}$ value is about 26% (15611/60000) and coincides with about 70% of the maximum change of the $R_{min}$ angle. After the peak, $R_{min}$ returns to approximately the value for the sample-free solution.

Figure 3B:
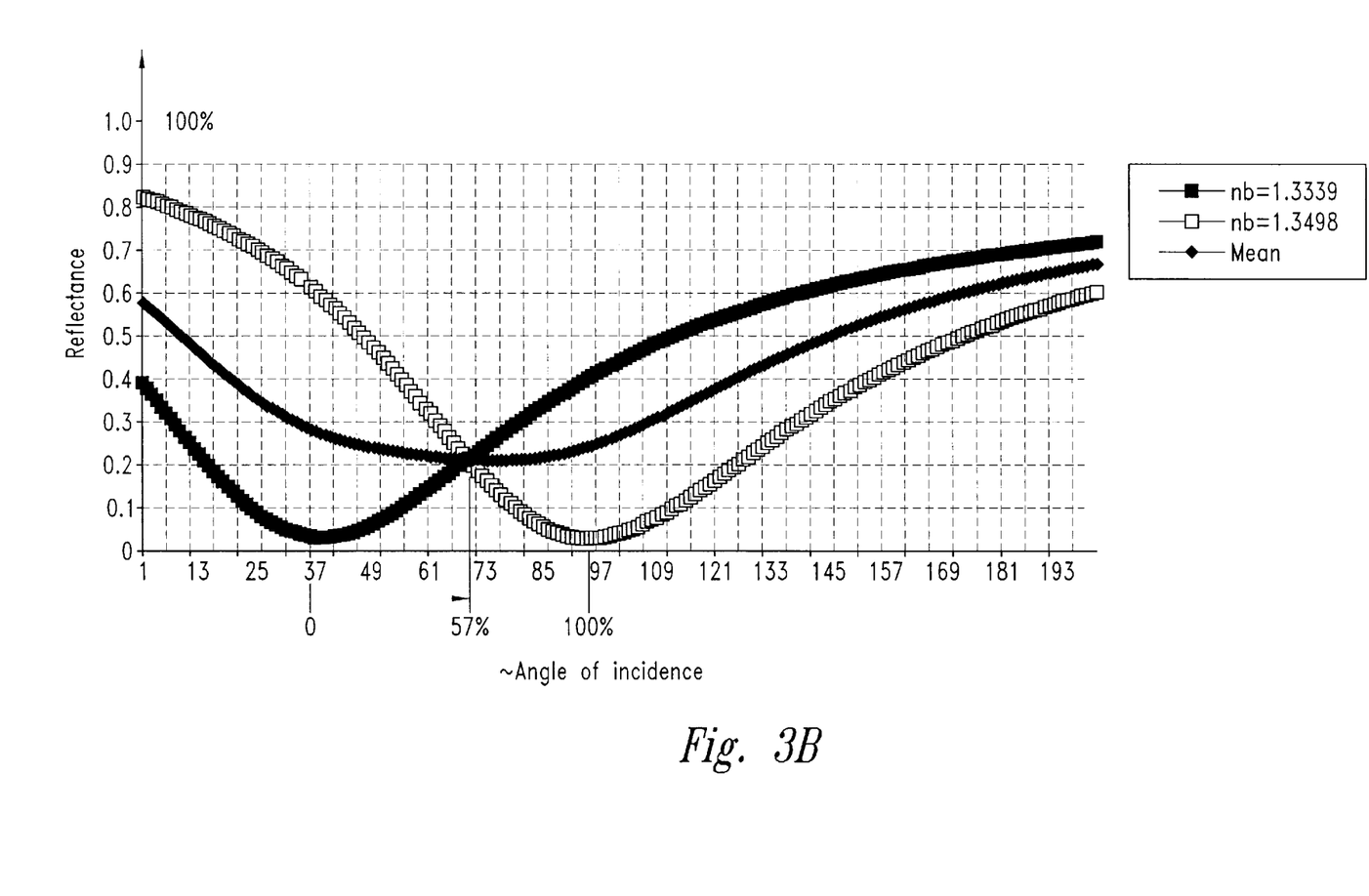

The above case represents the situation of a high sample concentration and two phases with well separated refractive index/reflectance curves. A calculation of $R_{min}$ for a two-phase film model with a transition via a coverage 0.57 of phase 1, n=1.3339, and coverage 0.43 of phase 2, n=1.3498, gave the results shown in FIG. 3b. The $R_{min}$ peak value was about 20%, coinciding with about 57% of the maximum change of the $R_{min}$ angle.

EXAMPLE 3

Figure 4A:
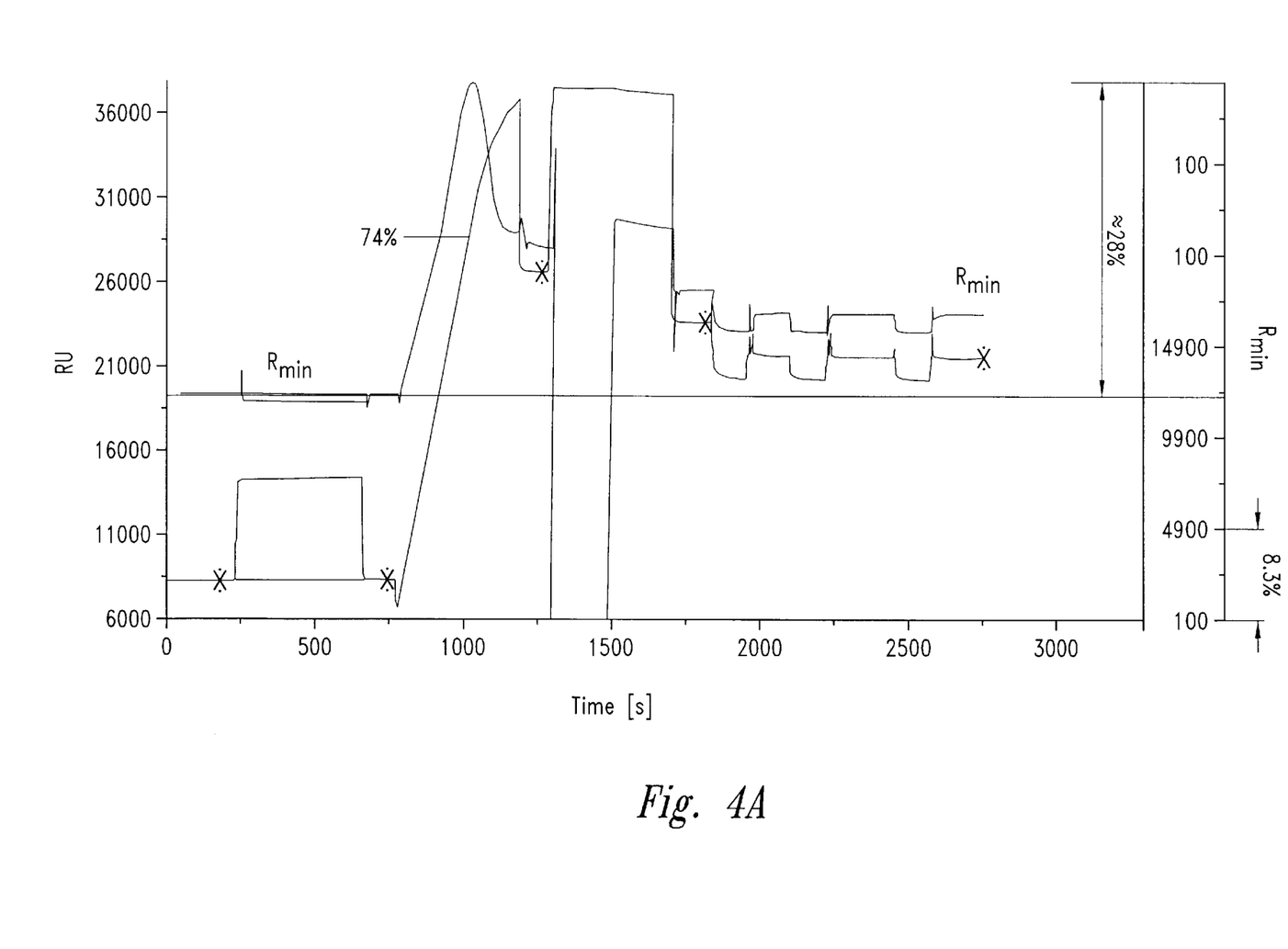
FIG. 4a is a similar overlay plot to that of FIG. 3a of a sensorgram (SPR response vs time) and a reflectance minimum vs time curve for the interaction of monoclonal antibody with immobilized rabbit antimouse IgG but where the interaction causes a permanent heterogeneity in the sensing surface due to aggregate formation.

In analogous manner to Example 1, a sensor surface was immobilized with rabbit antimouse IgG (RAMFc) of another batch and the interaction with the surface was studied at a flow rate of 5 μl/min. The sensorgram and the reflectance minimum ($R_{min}$) curve obtained are shown in FIG. 4a. As appears from the figure, the peak of the $R_{min}$ value is about 28% (16900/60000) and coincides with about 74% of the maximum change of the $R_{min}$ angle. After the peak, $R_{min}$ does not return to the value for the sample-free solution but is stabilized at a higher level, indicating a permanent heterogeneity within the sensed surface layer volume. Particle precipitation (RAMFc aggregate formation) in the sample solution was also detected by a separate independent method.

The above case represents the situation of a high sample concentration and particle precipitation, two phases with well separated refractive index/reflectance curves and a particulate surface film structure. A calculation of the corresponding $R_{min}$ for a two-phase film model with a transition via a coverage 0.6 of phase 1, n=1.3425, and a coverage 0.4 of phase 2, n=1.3512, gave the results shown in FIG. 4b. The $R_{min}$ peak value was about 23%, coinciding with about 79% of the maximum change of the $R_{min}$ angle at a coverage 1 of phase 2.

Figure 4B:
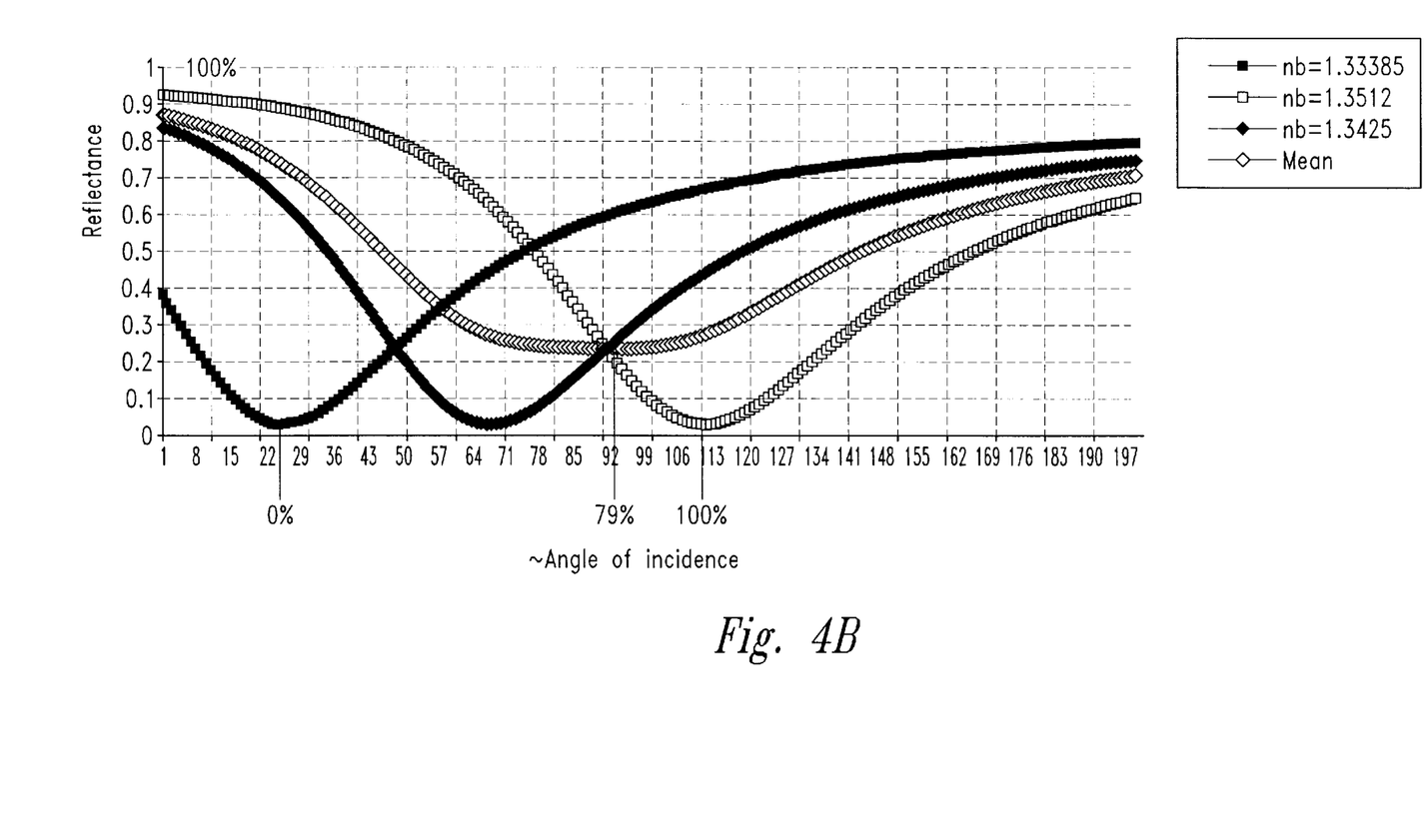
Figure 4C:
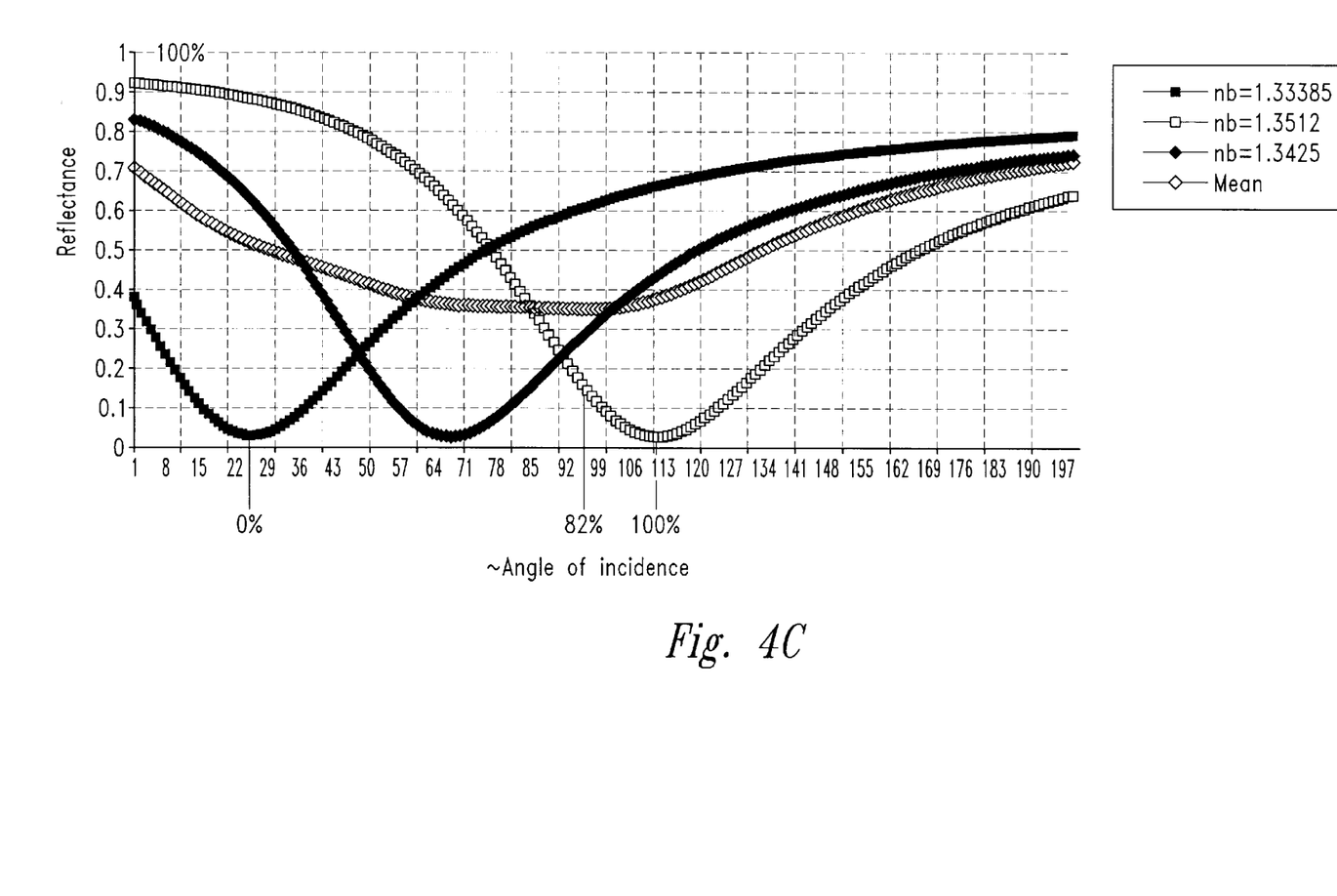

A corresponding calculation of $R_{min}$ for a three-phase film with a transition via a coverage 0.33 of phase 1, n=1.3339, a coverage 0.33 of phase 2, n=1.3425, and a coverage 0.33 of phase 3, n=1.3512, gave the results shown in FIG. 4c. The $R_{min}$ peak value was about 35%, coinciding with about 82% of the maximum change of the $R_{min}$ angle.

While none of the above two calculation models gave results corresponding to the experimental data, they correspond sufficiently well to demonstrate that it is possible to fit a greater number of phases of respective refractive indices as well as a distribution of surface coverage to simulate experimental results.

We claim:

1. A method of analyzing a chemical or physical interaction taking place in a film layer at an optical sensor surface when the film layer is contacted with a fluid sample containing a species capable of interacting with the film layer, wherein the interaction is monitored by determining the refractive index of the film layer through a light-intensity signal producing technique that involves measuring the relationship between a parameter associated with the incident or reflected light and one of the minimum, the maximum and the centroid of the light intensity signal curve, wherein the method comprises the step of monitoring the variation of the light intensity signal value at the minimum, maximum or centroid with time to determine at least one of (i) the degree of homogeneity of sample species concentration in the sensed film layer volume to determine therefrom when the interaction is mass transport limited and when the interaction is kinetically controlled; and (ii) the degree of resulting homogeneity/heterogeneity in the sensed film layer volume during or after the interaction.

2. The method according to claim 1, wherein the fluid sample is a liquid.

3. The method according to claim 1 or 2, further comprising the step of determining from the monitoring of the light intensity signal value the time interval or intervals when the interaction is kinetically controlled, and from the relationship between refractive index and time measured during the interval or intervals, determining the association or dissociation constants for the interaction of the sample species with the surface layer.

4. The method according to claim 3, wherein the step of determining the association or dissociation constants, is automatically initiated when the interaction is kinetically controlled.

5. The method according to claim 3, wherein the step of determining from the monitoring of the light intensity signal value the time interval or intervals when the interaction is mass transfer limited, and from the relationship between refractive index and time measured during the interval or intervals, determining the concentration of the sample species.

6. The method according to claim 3 further comprising determining both the concentration of the sample species and the association or dissociation constants.

7. The method according to claim 1, wherein the homogeneity/heterogeneity relates to one or more of the physical condition, the thermodynamic condition and the chemical condition of the film layer.

8. The method according to claim 7, wherein the homogeneity/heterogeneity in the surface film layer is selected from protein aggregates caused by precipitation, agglutination or flocculation reactions; membrane complexes; macromolecular product complexes caused by enzymatic reactions; or cellular product complexes.

9. The method according to claim 8, further comprising measuring the sample species concentration related to the measured homogeneity/heterogeneity.

10. The method according to claim 9, further comprising pre-immobilizing a reactant ligand to the sensor surface film layer and determining any heterogeneity in the resulting ligand concentration or structure therein.

11. The method according to claim 1, further comprising monitoring the halfwidth of the light intensity signal curve versus time to obtain additional information on the degree of resulting homogeneity/heterogeneity within the sensed ilm volume.

12. The method according to claim 1, wherein the light intensity producing signal technique is based on reflectometry, reflection ellipsometry, reflection interferometry or resonant guided mode detection in a waveguide.

13. The method according to claim 12, wherein the light intensity producing signal technique is an internal or external reflection technique, wherein the internal reflection technique relates to surface plasmon resonance, Brewster angle, critical angle, ellipsometry, or resonant mode coupling, and wherein the external reflection technique relates to Brewster angle or ellipsometry.

14. The method according to claim 13, wherein the internal or external reflection technique involves measurement of the wavelength, incident angle or polarization state.

15. method according to claim 14, wherein the interaction is monitored by using at least two different wavelengths and a fixed incident angle.

16. The method according to claim 14, wherein the interaction is monitored by using at least two different wavelengths and at least two different incident angles.

17. The method according to claim 14, wherein the interaction is monitored by using a continuous scan of a predetermined incident angle or wavelength range.

18. The method according to claim 14, wherein the interaction is monitored by using at least two different polarization states and a fixed incident angle and wavelength.

19. The method according to claim 14, wherein the interaction is monitored by using a continuous scan of a predetermined polarization state range.

20. The method according to claim 13, wherein the interaction is monitored hy using internal reflection data measured at a number of wavelengths to determine the state of homogeneity/heterogeneity in the direction of the penetration depth of the evanescent wave.

21. The method according to claim 1, wherein the interaction is monitored with two or more sensor surfaces simultaneously using a single light beam.

22. The method according to claim 1, wherein the fluid sample is contacted with the film layer in a liquid flow.

* * * * *

UNITED STATES PATENT AND TRADEMARK OFFICE
CERTIFICATE OF CORRECTION

PATENT NO : 6,127,183
DATED : Oct. 3, 2000
INVENTOR(S) : Ivarsson et, al.

It is certified that errors appear in the above-identified patent and that said Letters Patent are hereby corrected as shown below:

Claim 11, column 13, line 6 "sensed ilm" should read --sensed film--.

Signed and Sealed this

Fifteenth Day of May, 2001

NICHOLAS P. GODICI

Attest:

Attesting Officer     Acting Director of the United States Patent and Trademark Office

UNITED STATES PATENT AND TRADEMARK OFFICE
CERTIFICATE OF CORRECTION

PATENT NO.    : 6,127,183
DATED         : October 3, 2000
INVENTOR(S)   : Ivarsson et al.

It is certified that error appears in the above-identified patent and that said Letters Patent is hereby corrected as shown below:

Column 13,
Line 6, "sensed ilm" should read -- sensed film --.

Signed and Sealed this

Fifth Day of October, 2004

JON W. DUDAS
*Director of the United States Patent and Trademark Office*